United States Patent [19]
Lillig et al.

[11] Patent Number: 5,258,536
[45] Date of Patent: Nov. 2, 1993

[54] (2-METHYL-3-CHLOROPROPYL)-CYCLOHEXYL-DIALKOXYSILANES

[75] Inventors: Bernhard Lillig; Claus-Dietrich Seiler, both of Rheinfelden, Fed. Rep. of Germany

[73] Assignee: Hüls Aktiengesellschaft, Marl, Fed. Rep. of Germany

[21] Appl. No.: 29,183

[22] Filed: Mar. 10, 1993

[30] Foreign Application Priority Data

Apr. 29, 1992 [DE] Fed. Rep. of Germany ....... 4214134

[51] Int. Cl.$^5$ .............................................. C07F 7/18
[52] U.S. Cl. ..................................... 556/446; 556/485
[58] Field of Search ................................. 556/485, 446

[56] References Cited

U.S. PATENT DOCUMENTS 4,102,670 7/1978 Foery et al. .................... 556/485 X
5,073,644 12/1991 Deschler et al. ................ 556/485 X

*Primary Examiner*—Paul F. Shaver
*Attorney, Agent, or Firm*—Felfe & Lynch

[57] ABSTRACT

Novel (2-methyl-3-chloropropyl)-cyclohexyl-dialkoxysilanes are prepared by reacting a (2-methyl-3-chloropropyl)-cyclohexyldichlorosilane with a corresponding alcohol. The novel compounds are useful for the modification of silicones.

7 Claims, No Drawings

(2-METHYL-3-CHLOROPROPYL)-CYCLOHEXYL-DIALKOXYSILANES

FIELD OF THE INVENTION

This invention relates to novel (2-methyl-3-chloropropyl)-cyclohexyl-dialkoxysilanes as well as to a method of preparing these compounds.

OBJECTS OF THE INVENTION

An object of the present invention is to provide novel difunctional diorganic silane compounds, especially those compounds whose molecule contains, in addition to a non-reactive radical such as an alkyl or cycloalkyl group, a radical which comprises a key atom, preferably a chlorine atom, for the introduction of functional groups. The introduction of the desired functional groups can be effected after the incorporation of the molecule containing the key atom into siloxane chains or else into the starting compound.

Other objects and advantages of the present invention will become apparent as the description thereof proceeds.

DESCRIPTION OF THE INVENTION

The above object is achieved by synthesizing previously unknown (2-methyl-3-chloropropyl)-cyclohexyl-dialkoxysilanes of the formula

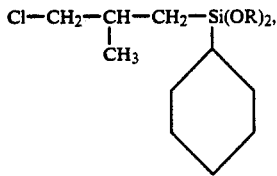

(I)

wherein R is alkyl of 1 to 6 carbon atoms the carbon chain of which may optionally be interrupted by oxygen atoms.

The novel dialkoxysilanes of the formula I may be prepared by reacting (2-methyl-3-chloropropyl)-cyclohexyl-dichlorosilane with an alcohol of the formula

*HOR* where R has the meanings previously defined. In the case of batch esterification of the (2-methyl-3-chloropropyl)-cyclohexyldichlorosilane, the alcohol is introduced into the chlorosilane while stirring, and the chlorosilane is reacted stepwise accompanied by driving out the hydrogen chloride which is formed up to the last esterification stage. For this purpose the system is brought in the final esterification stage up to the boiling point. The esterification may also be performed in the presence of solvents, which may be present in any desired concentration. Suitable solvents are hydrocarbons, such as heptane or toluene, but also chlorinated hydrocarbons such as dichloroethylene or trichloroethylene, which are especially effective. A solvent is preferably employed when the alcohol reactant is one which contains oxygen atoms in the alkyl chain. The boiling point of the system can be reduced by application of a vacuum.

The continuous production of the novel (2-methyl-3-chloropropyl)-cyclohexyl-dialkoxysilanes is performed by reacting the chlorosilane with the alcohol and removing the hydrogen chloride formed by the reaction in a reactor and a column connected thereto through which gaseous alcohol flows and into the top of which the reaction mixture leaving the reactor is introduced. The end product is withdrawn from the bottom end of the column. In this process the chlorosilane is introduced in fluid form into the reactor, the corresponding stoichiometric amount of alcohol is introduced in gaseous form into the bottom part of the column, and alcohol condensed at the top of the column is recycled into the reactor. The continuous process is preferred for the esterification of chlorosilane with short-chain alcohols.

The novel (2-methyl-3-chloropropyl)-cyclohexyl-dialkoxysilanes of the present invention are useful for modifying silicones.

The following examples illustrate the present invention and will enable others skilled in the art to understand it more completely. It should be understood, however, that the invention is not limited solely to the particular examples given below.

EXAMPLE 1

(2-Methyl-3-chloropropyl)-cyclohexyl-dimethoxysilane

A 6-liter four-necked round-bottom flask was placed into a mushroom heater and equipped with a stirrer, a reflux condenser, a dropping funnel and a thermometer. 1367 g (5 mols) of (2-methyl-3-chloropropyl)-cyclohexyl-dichlorosilane together with 900 ml of trichloroethylene were introduced into the flask and heated to the boiling point while stirring. 160 g (5 mols) of methanol were introduced below the liquid surface over a period of 90 minutes. The system was maintained for another 20 minutes at the reflux temperature, and then 160 g (5 mols) of methanol were again added over a period of 90 minutes. Thereafter, the reaction mixture was refluxed for 20 minutes more, and then the crude product was worked up by vacuum distillation.

The structure of the reaction product was elucidated by elemental and gas chromatographic/mass spectrometric (GC/MS) analysis.

| Molecular weight: | Theory | 264.5 g/mol |
|---|---|---|
| | Found | 267.4 g/mol |
| Elemental analysis: | Theory | Found |
| C | 54.5 wt. % | 54.7 wt. % |
| H | 9.4 wt. % | 9.3 wt. % |
| Si | 10.6 wt. % | 10.4 wt. % |
| Cl | 13.4 wt. % | 13.3 wt. % |
| O | 12.1 wt. % | 12.3 wt. % |

Accordingly, the reaction product had the following structural formula:

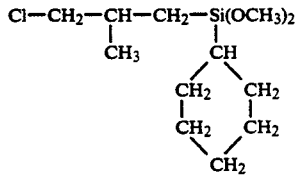

EXAMPLE 2

(2-Methyl-3-chloropropyl)-cyclohexyl-di(2-methoxyethoxy)silane

The same apparatus as that described in Example 1 was used. 1367 g (5 mols) of 2-methyl-3-chloropropyl)- cyclohexyl-dichlorosilane were introduced into the reactor together with 900 of 1,2-dichloroethylene. The esterification was performed as described in Example 1. Instead of methanol, however, two portions of 380 g (5 mols) each of 2-methoxy-ethanol were used.

The crude product thus obtained was worked up by vacuum distillation. The structure of the reaction product was elucidated by elemental and GC/MS analysis.

| Molecular weight: | Theory | 352.5 g/mol |
| --- | --- | --- |
| | Found | 356.2 g/mol |
| Elemental analysis: | Theory | Found |
| C | 54.5 wt. % | 54.8 wt. % |
| H | 9.4 wt. % | 9.5 wt. % |
| Si | 7.9 wt. % | 7.8 wt. % |
| Cl | 10.1 wt. % | 10.1 wt. % |
| O | 18.1 wt. % | 17.8 wt. % |

Accordingly, the reaction product had the following structural formula:

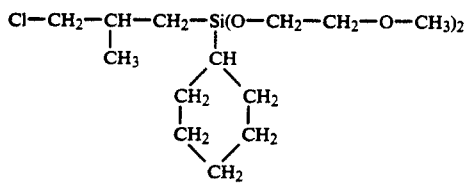

EXAMPLE 3

(2-Methyl-3-chloropropyl)-cyclohexyl-dipropoxysilane

The same apparatus as that described in Example 1 was used. 1367 g (5 mols) of (2-methyl-3-chloropropyl)-cyclohexyl-dichlorosilane were introduced into the flask. At a starting temperature of 60° C., 300 g (5 mols) of n-propanol were added at a uniform rate over a period of 140 minutes. Thereafter the mixture was heated in 120 minutes to 145° C., accompanied by the escape of dissolved hydrogen chloride. The system was from this time forward evacuated to such an extent that it began to boil at a sump temperature of 145° C. An additional 300 g (5 mols) of n-propanol were introduced into the boiling reaction mixture over a period of 140 minutes. The reaction mixture was allowed to react for 35 minutes more, and then the crude product was worked up by vacuum distillation.

The structure of the reaction product was elucidated by elemental and GC/MS analysis.

| Molecular weight: | Theory | 320.5 g/mol |
| --- | --- | --- |
| | Found | 327.2 g/mol |
| Elemental analysis: | Theory | Found |
| C | 59.9 wt. % | 59.6 wt. % |
| H | 10.3 wt. % | 10.4 wt. % |
| Si | 8.7 wt. % | 8.5 wt. % |
| Cl | 11.1 wt. % | 11.3 wt. % |
| O | 10.0 wt. % | 10.2 wt. % |

Accordingly, the reaction product had the following structural formula:

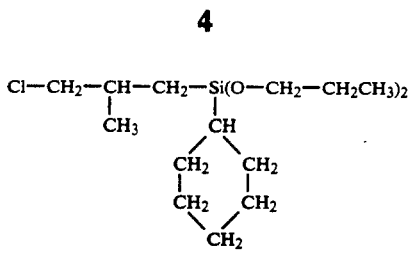

EXAMPLE 4

(2-Methyl-3-chloropropyl)-cyclohexyl-dihexoxysilane

The apparatus was identical to that described in Example 1. 1367 g (5 mols) of (2-methyl-3-chloropropyl)-cyclohexyl-dichlorosilane were introduced into the flask together with 900 ml of hexane. The esterification was performed as described in Example 1. However, in place of methanol, two portions of 510 g (5 mols) each of n-hexanol were used. The raw reaction product was worked up by distillation in vacuo. The structure of the reaction product was elucidated by elemental and GC/MS analysis.

| Molecular weight: | Theory | 404.5 g/mol |
| --- | --- | --- |
| | Found | 398.4 g/mol |
| Elemental analysis: | Theory | Found |
| C | 65.3 wt. % | 65.1 wt. % |
| H | 11.1 wt. % | 11.3 wt. % |
| Si | 6.9 wt. % | 7.0 wt. % |
| Cl | 8.8 wt. % | 8.6 wt. % |
| O | 7.9 wt. % | 8.0 wt. % |

Accordingly, the reaction product had the following structural formula:

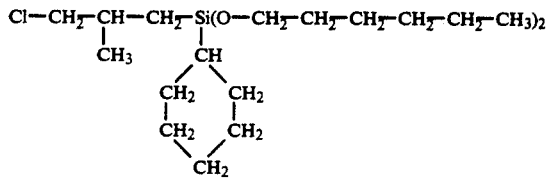

EXAMPLE 5

(2-Methyl-3-chloropropyl)-cyclohexyl-di-[2-(2-methoxy-ethoxy)-ethoxy]-silane

The apparatus was identical to that described in Example 1. 1367 g (5 mols) of (2-methyl-3-chloropropyl)-cyclohexyl-dichlorosilane together with 900 ml of hexane were introduced into the flask. The esterification procedure was carried out in the same manner as described in Example 1. However, instead of methanol, two portions of 600 g (5 mols) each of methyldiglycol[2-(2-methoxy-ethoxy)-ethanol] were used. The raw reaction product was worked up by vacuum distillation. The structure of the reaction product was elucidated by elemental and GC/MS analysis.

| Molecular weight: | Theory | 440.5 g/mol |
| --- | --- | --- |
| | Found | 444.3 g/mol |
| Elemental analysis: | Theory | Found |
| C | 54.5 wt. % | 54.7 wt. % |
| H | 9.3 wt. % | 9.1 wt. % |
| Si | 6.4 wt. % | 6.3 wt. % |
| Cl | 8.0 wt. % | 8.2 wt. % |

| | | |
|---|---|---|
| -continued | | |
| O | 21.8 wt. % | 21.7 wt. % |

Accordingly, the reaction product had the following structural formula:

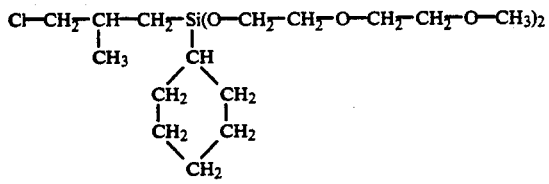

EXAMPLE 6
(2-Methyl-3-chloropropyl)-cyclohexyl-diethoxysilane 10 liters of (2-methyl-3-chloropropyl)-cyclohexyldiethoxysilane were introduced into a 40-liter reactor equipped with a stirrer, two immersion tubes and a brine-operated heat exchanger. 80 mols per hour of ethanol were introduced in gaseous form into the bottom part of a column through a quantity-controlled flow meter. The column had a length of 5 m and an inside diameter of 80 mm and was filled with 8×8 mm Raschig rings. Pure target product was placed into the column reservoir and the reservoir temperature was maintained at 140° C. Unreacted alcohol which condensed at the top of the column was fed through an immersion tube into the reactor which was kept at a temperature of 60° C. 40 mols of (2-methyl-3-chloropropyl)-cyclohexyl-dichlorosilane were metered through a second quantity-controlled flow meter into the reactor by way of the second immersion tube. Crude reaction product was continuously removed from the reactor and fed into the top of the column in countercurrent fashion against the ascending alcohol vapors. The target product was continuously withdrawn from the reservoir of the column.

The structure of the reaction product was elucidated by elemental and GC/MS analysis.

| Molecular weight: | Theory | 292.5 g/mol |
|---|---|---|
| | Found | 287.1 g/mol |
| Elemental analysis: | Theory | Found |
| C | 57.4 wt. % | 57.7 wt. % |
| H | 9.9 wt. % | 10.2 wt. % |

| | | |
|---|---|---|
| -continued | | |
| Si | 9.6 wt. % | 9.3 wt. % |
| Cl | 12.2 wt. % | 12.0 wt. % |
| O | 10.9 wt. % | 10.8 wt. % |

Accordingly, the reaction product had the following structural formula:

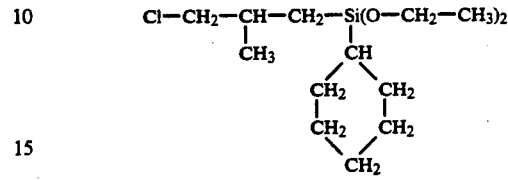

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A (2-methyl-3-chloropropyl)-cyclohexyl-dialkoxysilane of the formula:

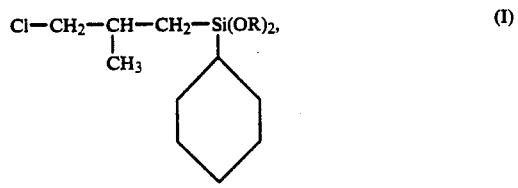

wherein R is alkyl of 1 to 6 carbon atoms which may optionally be interrupted by oxygen atoms.

2. The compound of claim 1, which is (2-methyl-3-chloropropyl)-cyclohexyl-dimethoxysilane.

3. The compound of claim 1, which is (2-methyl-3-chloropropyl)-cyclohexyl-di(2-methoxy-ethoxy)silane.

4. The compound of claim 1, which is (2-methyl-3-chloropropyl)-cyclohexyl-dipropoxysilane.

5. The compound of claim 1, which is (2-methyl-3-chloropropyl)-cyclohexyl-dihexoxysilane.

6. The compound of claim 1, which is (2-methyl-3-chloropropyl)-cyclohexyl-di[2-(2-methoxy-ethoxy)ethoxy]silane.

7. The compound of claim 1, which is (2-methyl-3-chloropropyl)-cyclohexyl-diethoxysilane.

* * * * *